US008460175B2

(12) United States Patent
Jo et al.

(10) Patent No.: US 8,460,175 B2
(45) Date of Patent: Jun. 11, 2013

(54) ENDOSCOPE MANIPULATOR FOR MINIMALLY INVASIVE SURGERY

(75) Inventors: Yung-Ho Jo, Gyeonggi-do (KR);
Kwang-Gi Kim, Gyeonggi-do (KR);
Kyoung-Won Nam, Gyeonggi-do (KR);
Young-Woo Kim, Seoul (KR)

(73) Assignee: National Cancer Center, Gyeonggi-do (KR)

( * ) Notice: Subject to any disclaimer, the term of this patent is extended or adjusted under 35 U.S.C. 154(b) by 727 days.

(21) Appl. No.: 12/589,439

(22) Filed: Oct. 23, 2009

(65) Prior Publication Data
US 2010/0274078 A1    Oct. 28, 2010

(30) Foreign Application Priority Data

Apr. 27, 2009    (KR) .................. 10-2009-0036311

(51) Int. Cl.
*A61B 1/00*          (2006.01)
(52) U.S. Cl.
USPC ............................................ 600/102; 901/15
(58) Field of Classification Search
USPC ........ 600/102, 15; 606/130; 700/253; 901/15
See application file for complete search history.

(56) References Cited

U.S. PATENT DOCUMENTS

| 3,587,872 | A | * | 6/1971 | Pauly et al. ................... 414/732 |
| 4,068,156 | A | * | 1/1978 | Johnson et al. .............. 318/575 |
| 4,273,506 | A | | 6/1981 | Thomson |
| 4,815,006 | A | | 3/1989 | Andersson |
| 4,863,133 | A | * | 9/1989 | Bonnell ................... 248/280.11 |
| 5,159,249 | A | * | 10/1992 | Megherbi ................... 318/568.1 |
| 5,228,429 | A | | 7/1993 | Hatano |
| 5,872,892 | A | | 2/1999 | Brown |
| 5,876,325 | A | * | 3/1999 | Mizuno et al. ............... 600/102 |

(Continued)

FOREIGN PATENT DOCUMENTS

| KR | 10-2004-0103212 A | 12/2004 |
| KR | 1020070023738 A | 2/2007 |
| KR | 10-2009-0119366 A | 11/2009 |

OTHER PUBLICATIONS

Mitsuishi, Mamoru et al.; "Development of a Remote Minimally-Invasive Surgical System with Operational Environment Capability"; Proceeding 2003 IEEE on Robotics and Automation; Taipei, Taiwan, Sep. 14-19, 2003.*

(Continued)

*Primary Examiner* — Clayton E LaBalle
*Assistant Examiner* — Kevin Butler
(74) *Attorney, Agent, or Firm* — Hamilton, Brook, Smith & Reynolds, P.C.

(57) ABSTRACT

According to endoscope manipulator for MIS capable of overcoming disadvantages of multiaxial endoscope manipulator including conventional robot arm and providing compact and light-weight structure to obtain maximum activity space for medical staff, multi-joint arm is configured so that movement of all joints from base link to tip link is manually locked-unlocked by user and not controlled by motors. Endoscope mounted on end of multi-joint arm is manipulated using motors to enable movement of three-degrees of freedom, thereby accomplishing compact and light-weight endoscope manipulator. Tube of endoscope can be press-fitted onto tip of multi-joint arm, and three-axis movement function for vertical, lateral and forward/backward conveyance of endoscope is implemented in tip of multi-joint arm. Since external manual joints are not moved during operation, disturbance or restriction to activities of medical staff can be minimized. One-click button function of readily and rapidly attaching/detaching endoscope to/from endoscope manipulator can increase convenience of use.

19 Claims, 15 Drawing Sheets

U.S. PATENT DOCUMENTS

| | | | | |
|---|---|---|---|---|
| 5,907,664 | A * | 5/1999 | Wang et al. | 700/251 |
| 6,432,112 | B2 * | 8/2002 | Brock et al. | 606/130 |
| 6,853,879 | B2 * | 2/2005 | Sunaoshi | 700/253 |
| 2004/0015053 | A1 | 1/2004 | Bieger | |
| 2010/0274079 | A1 | 10/2010 | Kim et al. | |

OTHER PUBLICATIONS

Mayer et al; The Endo Par System for Minimally Invasive Robotic Surgery; Proceedings of 2004 Intl Conference Intelligent Robots and Systems; Sendai, Japan, Sep. 28-Oct. 2, 2004.*

Oura et al; Development of MRI Compatible Versatile Manipulator for Minimally Invasive Surgery; Waseda University; Tokyo, Japan.*

Guillaume Morel, "Applications of Force Feedback in Medical and Surgical Robotics", Euron Summer School on Medical Robotics, University Pierre et Marie Curie, CNRS, Paris, France, Sep. 2006.*

Peirs et Al., A Miniature Manipulator for Integration in a Self-Propelling Endoscope; Elsevier; Dec. 19, 2000.*

Peter-John Christiane, Development of a minimally invasive robotic surgical manipulator (submission for masters); Department of Mechanical and Mechatronic Engineering University of Stellenbosch; Dec. 2008.*

Aaron Arthure Kracht; A Linear Base Articulated Robot Arm for Surgical Endoscopy (theseis for Master); North Carolina State University School of Engineering; 2006.*

Neil Munro, Ph.D., D.SC., Robot Manipulator Control Theory and Practice Second Edition, Marcel Dekker, Inc., 2004, Chapter 1 Commercial Robot Manipulators.*

U.S. non-final Office Action for U.S. Appl. No. 12/589,444, dated Aug. 10, 2012.

U.S. Notice of Allowance for U.S. Appl. No. 12/589,444, dated Jan. 2, 2013.

* cited by examiner

ENDOSCOPE MANIPULATOR FOR MINIMALLY INVASIVE SURGERY

CROSS-REFERENCE TO RELATED APPLICATION

This application claims priority to and the benefit of Korean Patent Application No. 2009-0036311, filed Apr. 27, 2009, the disclosure of which is incorporated herein by reference in its entirety.

BACKGROUND

1. Technical Field

The present invention relates to an apparatus for manipulating a position of an endoscope used for extending a viewing angle within a human body during minimally invasive surgery and natural orifice transluminal endoscopic surgery, and more particularly, to an endoscope manipulator capable of moving an endoscope in vertical, lateral and longitudinal directions in a compact and lightweight structure.

2. Discussion of Related Art

In general, conventional open surgery for patient treatments causes delay of post-surgical recovery for the patients due to a large incision area and thus a heavy loss of blood, and large scars remaining after the surgery have a negative impact on the patients' lives after the surgery. In order to overcome the above disadvantages of the conventional open surgery, in recent times, novel surgical techniques such as minimally invasive surgery (MIS), natural orifice transluminal endoscopic surgery (NOTES), etc., have been developed.

MIS is a surgical technique of incising and operating on a minimal area of a patient's body using a thin and long surgical instrument specifically configured to minimize an incision area for surgery. NOTES is a surgical technique of inserting a surgical instrument through a natural orifice (for example, the esophagus, the anus, the vagina, etc.) of a human body and conveying the surgical instrument to the operation area in the body to operate on the area without incising the patient's body in order to move the surgical instrument to the operation area in the body. Since MIS and NOTES require only a small incision area for operation and a loss of blood is remarkably less than that of the open surgery, a post-surgical recovery time for the patient is shortened and scarring is minimal. Therefore, in recent times, the number of MIS and NOTES operations has remarkably increased.

When MIS and NOTES are performed, a specifically devised endoscope is used in order to obtain a visual field of an operation area through a minimal incision. That is, the endoscope is a medical imaging device for MIS, in which a visual field of the interior of the patient's body cannot be directly obtained. Surgeons and nurses using MIS perform operations while viewing images of the surgical area obtained through the endoscope.

While performing MIS and NOTES, in order to maximally and accurately show a state of the operation area and movement of the surgical instrument in the patient's body, which are prone to change frequently, positions and visual fields of the endoscope must be continuously varied. In order to manipulate movement of the endoscope throughout the entire operation, movement of the endoscope is currently handled by an assistant surgical operator other than the surgeon, joining the operating team. However, when the exclusive operator who manipulates the endoscope separately joins the operating team, skilled medical operators are unnecessarily used and thus surgical operations are performed less frequently.

In order to solve these problems, in recent times, several endoscope manipulators have been developed to manipulate the endoscope without an exclusive operator. Most of the recently developed endoscope manipulators employ a method of manipulating movement of the endoscope using a robotic technique of a multi-axially controlled robot arm. When the endoscope is manipulated using the robot arm, the position and angle of the endoscope can be accurately adjusted through forward-reverse mechanical analysis of the robot arm. However, since all joints are controlled using motors, loads applied to the joints are increased toward the base joint, thus increasing the total size and weight. In addition, depending on necessity, when the joint of the robot arm is largely moved to adjust a posture of the endoscope, the large movement may disturb or restrict activities of medical staff.

SUMMARY

The present invention is directed to an endoscope manipulator for MIS capable of overcoming disadvantages of a multiaxial endoscope manipulator including a conventional robot arm and providing a compact and lightweight structure to obtain a maximum activity space for medical staff.

Additional aspects of the invention will be set forth in the description which follows, and in part will be apparent from the description, or may be learned by practice of the invention.

In an example embodiment, an endoscope manipulator for MIS includes: a multi-joint arm; a first rotary part coupled to an end of the multi-joint arm to be rotated about a center of a first rotary shaft; a first driver configured to drive rotation of the first rotary part; a second rotary part coupled to the first rotary part to be rotated about a second rotary shaft perpendicular to the first rotary shaft, and having an endoscope mounted thereon; and a second driver configured to drive rotation of the second rotary part.

In addition, the multi-joint arm may be provided as a multi-joint type manual link that can be locked or unlocked.

Further, one end of the first rotary part may be coupled to the first driver to be rotated about the first rotary shaft, and the other end of the first rotary part may be coupled to the second rotary part to be rotated about the second rotary shaft. For example, while the example embodiment shows that the first rotary part has a U-shaped structure in which the other end is bifurcated and rotatably coupled to both sides of the second rotary part, the shape is not limited thereto, and may be any of various shapes.

Furthermore, the first driver may include a first motor installed at an end of the multi-joint arm, and configured to laterally rotate the endoscope with respect to the first rotary shaft through rotation of the first rotary part.

In addition, the second rotary part may include a rotary bracket coupled to the first rotary part to be rotated about the second rotary shaft, and an endoscope mounting part coupled to the rotary bracket and on which the endoscope is mounted.

Further, the second rotary part may include a one-click attachment part to which the endoscope can be attached or detached by one click.

Furthermore, the one-click attachment part may include a one-click button body, onto which the tube of the endoscope is press-fitted, configured to selectively adhere or separate the tube of the endoscope to or from the conveyance roller upon one-click operation through raising/lowering thereof, and an elastic member configured to provide an elastic force to the one-click button body so that the tube of the endoscope is closely adhered to the conveyance roller. Here, the one-click button body may be installed in the second rotary part, and have a cylindrical shape having an endoscope insertion hole formed in a longitudinal direction thereof so that the tube of the endoscope is press-fitted thereinto and an upper surface partially exposed from the second rotary part. In addition, the elastic member may include at least one spring disposed between an outer diameter of the one-click button body positioned at an opposite side of the conveyance roller with respect to the tube of the endoscope and a lower surface of the second rotary part.

Further, the second driver may rotate the endoscope in a vertical direction with respect to the second rotary shaft through rotation of the second rotary part.

Furthermore, the second driver may include a second motor installed at the first rotary part, and a first gear configured to transmit a rotational force of the second motor to the second rotary shaft configured to rotatably pivot the first rotary part and the second rotary part. Here, the first gear may be a first worm gear including a worm installed at a rotary shaft of the second motor, and a worm wheel installed at the second rotary shaft to be engaged with the worm and rotated therewith. Here, the rotary shaft of the second motor may be disposed perpendicular to the second rotary shaft.

In addition, the endoscope manipulator for MIS in accordance with an example embodiment of the present invention may further include a third driver configured to drive straight conveyance of the endoscope press-fitted onto the second rotary part. Here, an example embodiment of the third driver may include a third motor installed at the second rotary part, a conveyance roller rotatably installed at the second rotary part and adhered to a tube of the endoscope to straightly convey the endoscope forward and backward, and a second gear configured to transmit a rotational force of the third motor to a rotary shaft of the conveyance roller. Here, the second gear may be a second worm gear including a worm installed at a rotary shaft of the third motor, and a worm wheel installed at the rotary shaft of the conveyance roller to be engaged with the worm and rotated therewith. Here, the rotary shaft of the third motor may be disposed perpendicular to the rotary shaft of the conveyance roller.

Further, another example embodiment of the third driver may include a third motor installed at the second rotary part, an endoscope conveyance tube, into which the tube of the endoscope is inserted and fastened, movably installed at the second rotary part forward and backward, and a second gear configured to transmit a rotational force of the third motor to straightly move the endoscope conveyance tube. The endoscope conveyance tube may have an elliptical or polygonal cross-section. Here, the second gear may include a rack gear formed at an outer diameter of the endoscope conveyance tube in a longitudinal direction thereof, and a pinion gear installed at a rotary shaft of the third motor to be engaged and rotated with the rack gear.

In another example embodiment, an endoscope manipulator for MIS includes: a first rotary part coupled to an end of a multi-joint arm to be rotated about a first rotary shaft; a second rotary part coupled to be rotated about a second rotary shaft perpendicular to the first rotary shaft, and coupled to straightly convey an endoscope forward and backward; and a one-click attachment part configured to detachably attach the endoscope to the second rotary part by one click.

Specific descriptions of other example embodiments will be apparent from the detailed description and the attached drawings.

BRIEF DESCRIPTION OF THE DRAWINGS

The above and other objects, features and advantages of the present invention will become more apparent to those of ordinary skill in the art by describing in detail example embodiments thereof with reference to the attached drawings, in which.

DETAILED DESCRIPTION OF EXAMPLE EMBODIMENTS

Figure 1:
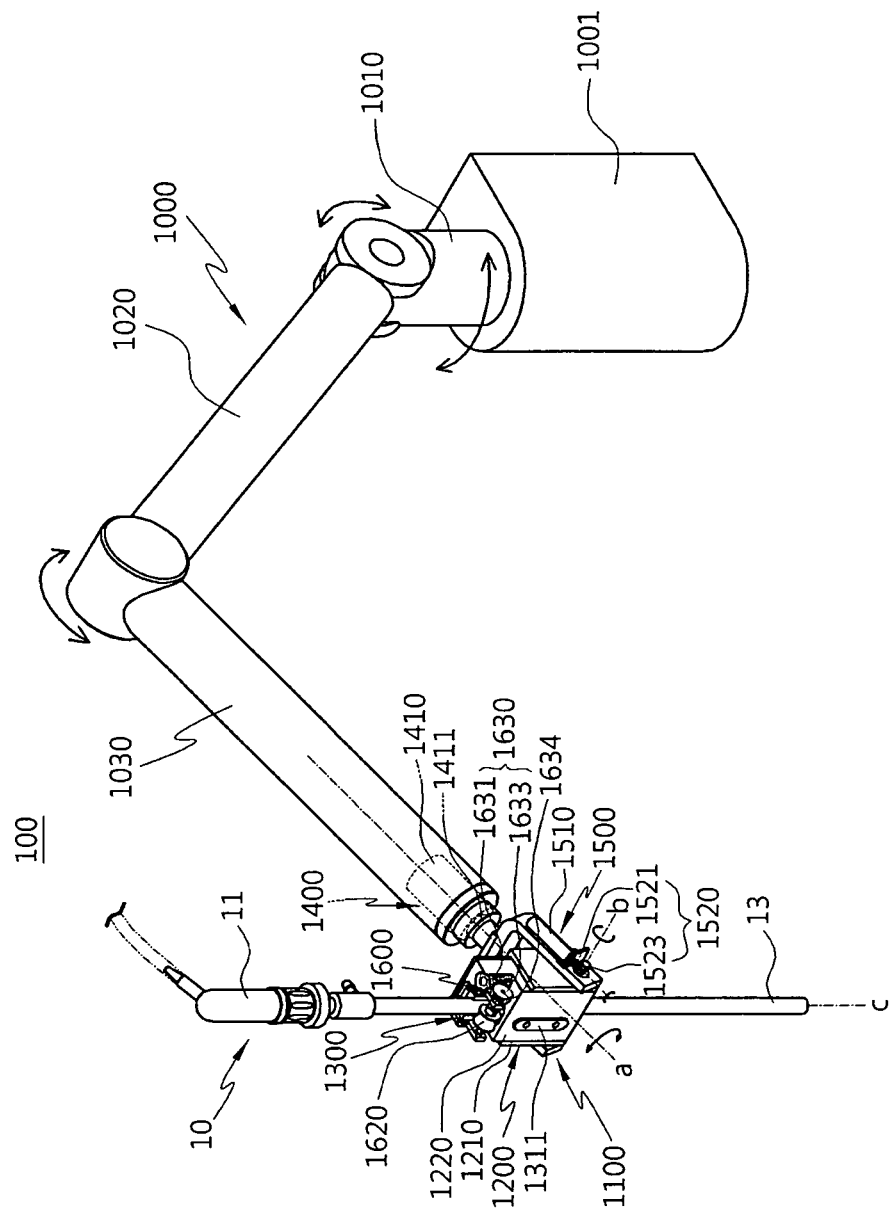
FIG. 1 is a perspective view of an endoscope manipulator for MIS according to one example embodiment of the present invention.

Hereinafter, example embodiments of the present invention will be described in detail. However, the present invention is not limited to the embodiments disclosed below, but can be implemented in various forms. The following embodiments are described in order to enable those of ordinary skill in the art to embody and practice the present invention. Like reference numerals designate like elements throughout the detailed description.

Hereinafter, an endoscope manipulator for MIS in accordance with an example embodiment of the present invention will be described with reference to the accompanying drawings. In the detailed description, if it is determined that description of conventional functions or constitutions may make the spirit of the invention unclear, detailed description thereof will be omitted.

Figure 2:
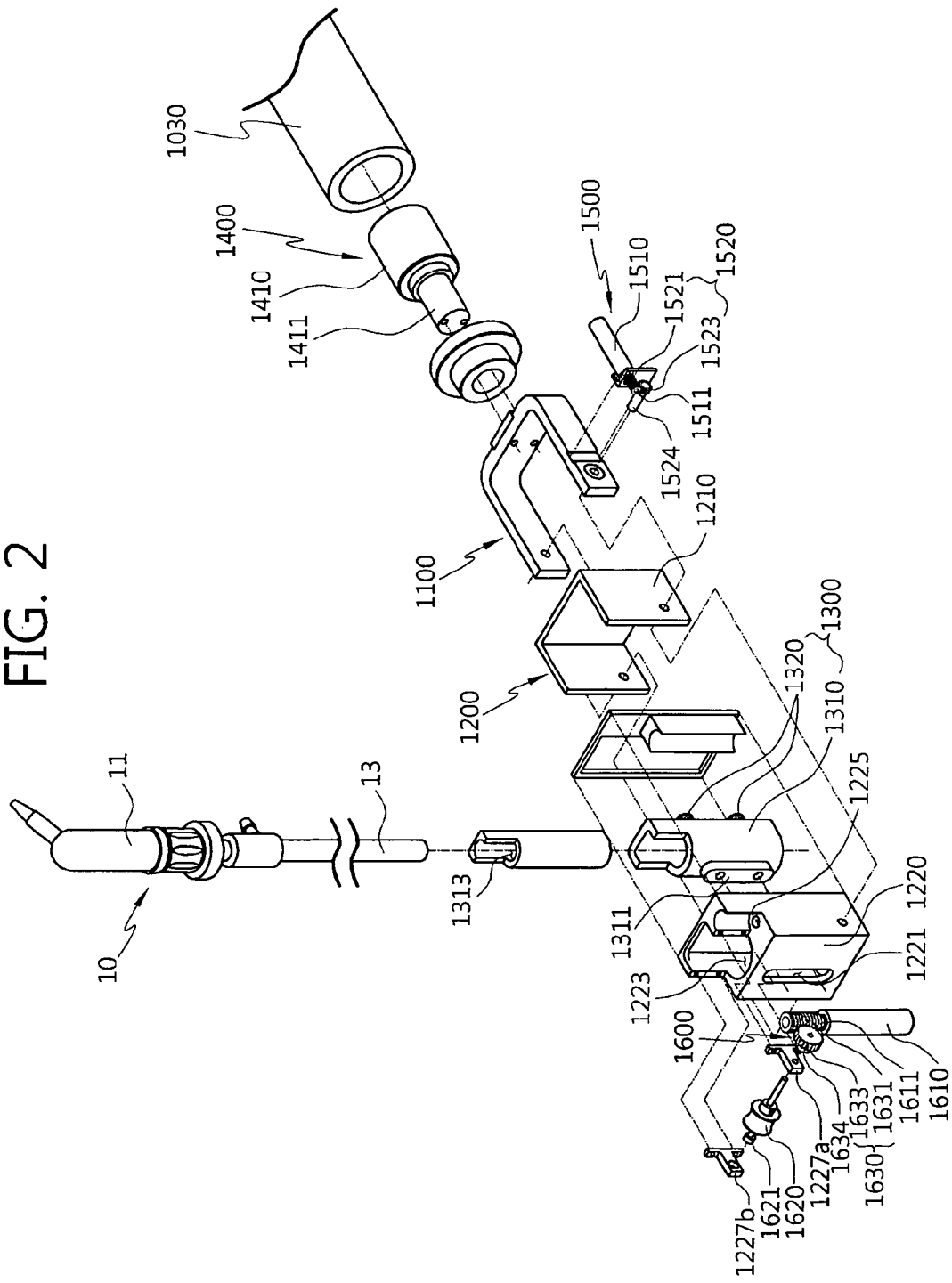
FIG. 2 is an exploded perspective view of the endoscope manipulator for MIS according to the present invention.
Figure 3:
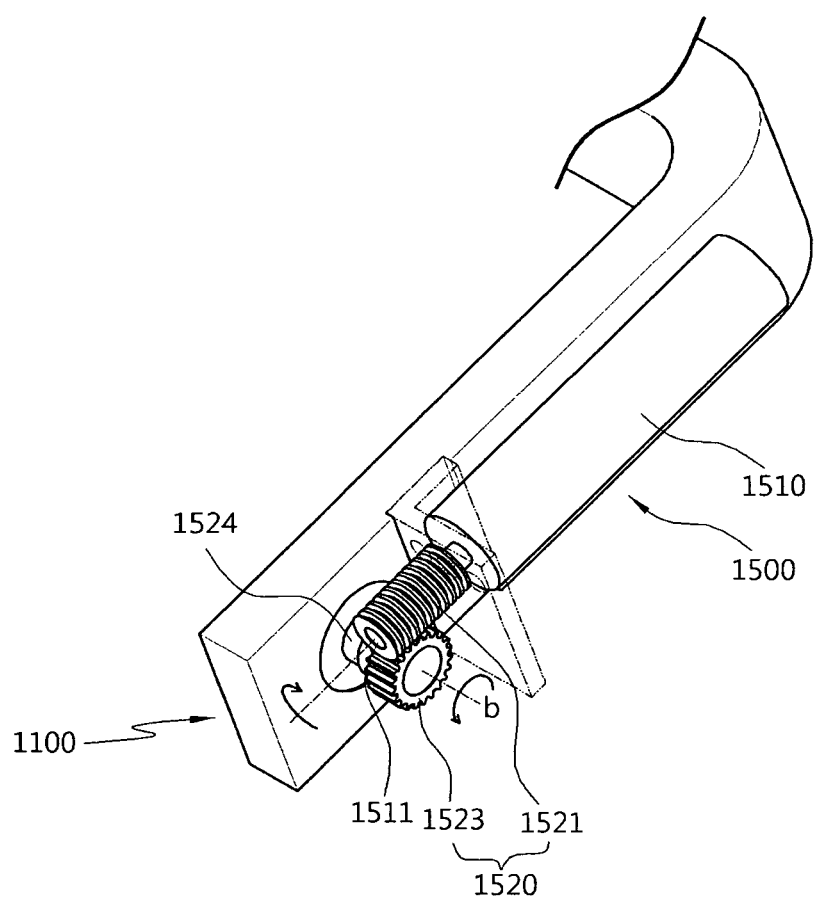
FIG. 3 is a perspective view specifically showing a second driver of FIG. 1.
Figure 4:
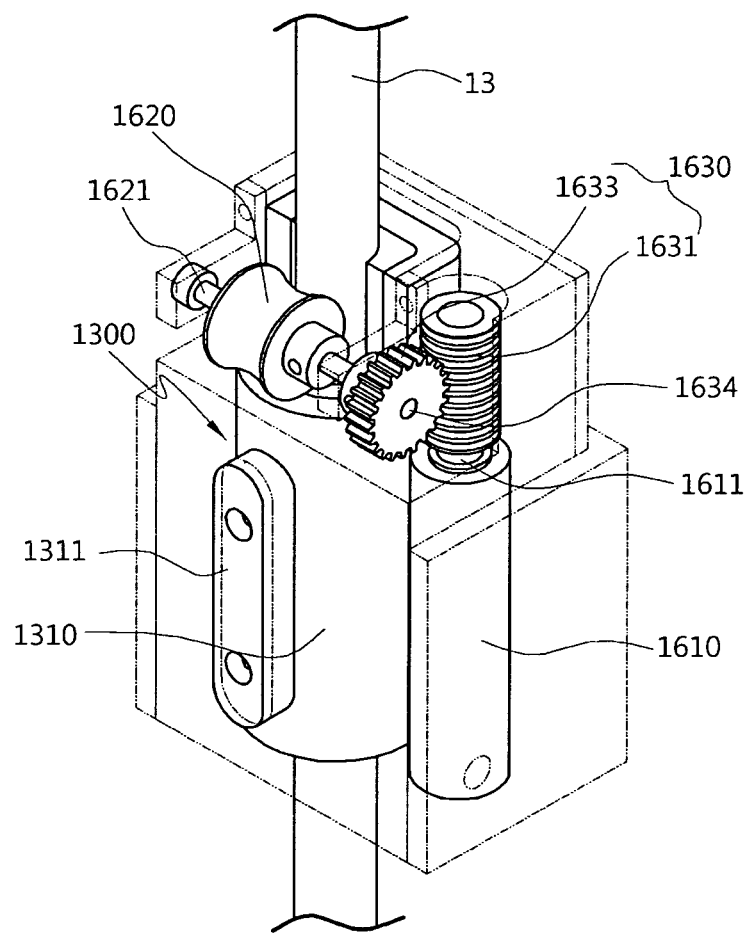
FIG. 4 is a perspective view specifically showing a third driver of FIG. 1.
Figure 5:
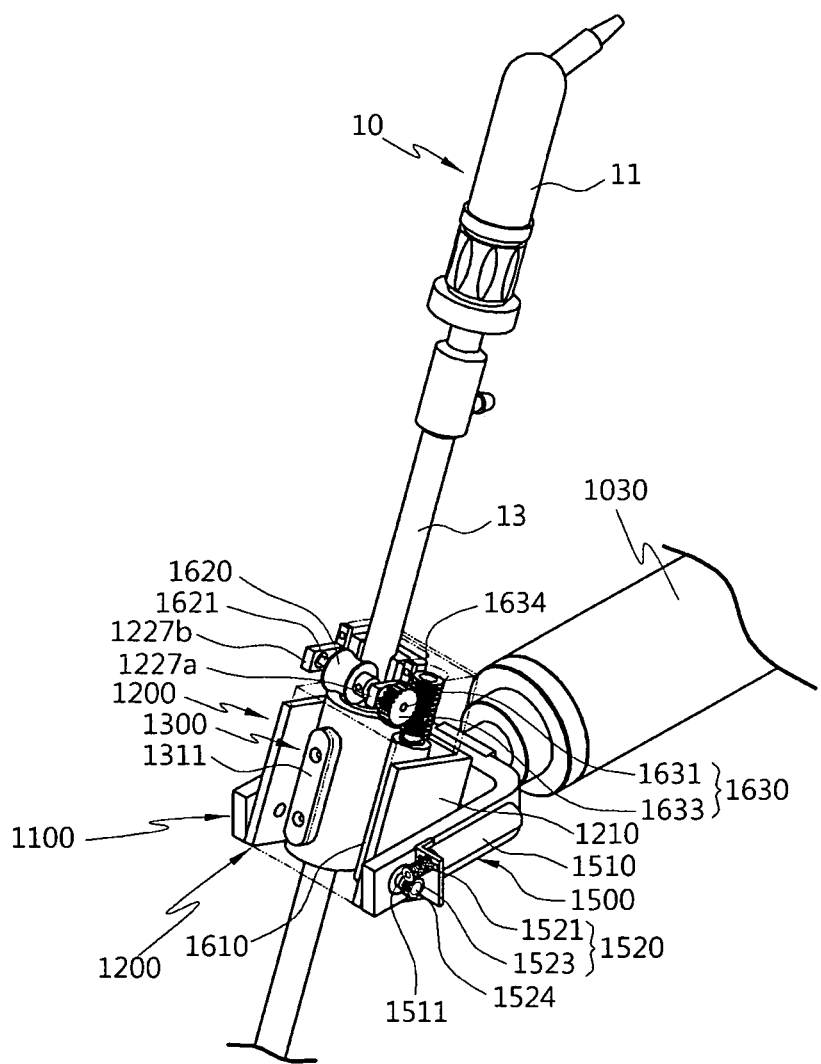
FIG. 5 is a perspective view specifically showing an endoscope mounting part of a second rotary part of FIG. 1.
Figure 6:
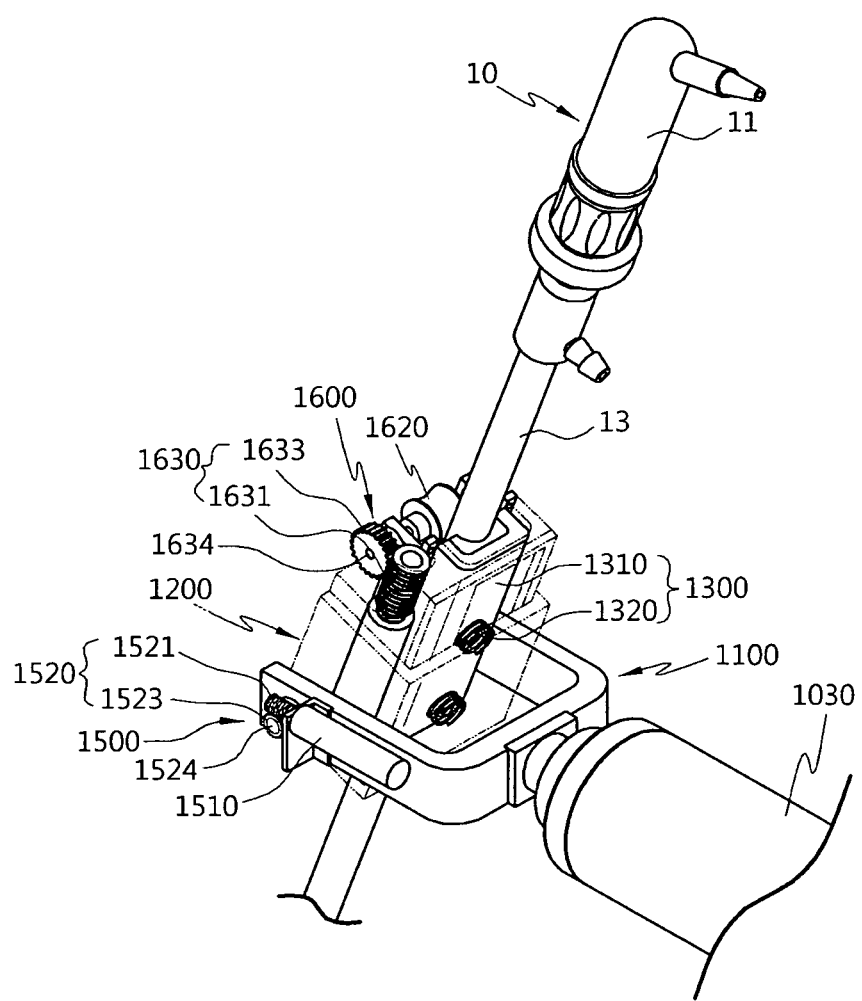
FIG. 6 is a perspective view specifically showing a one-click attachment part of the second rotary part of FIG. 5.
Figure 7:
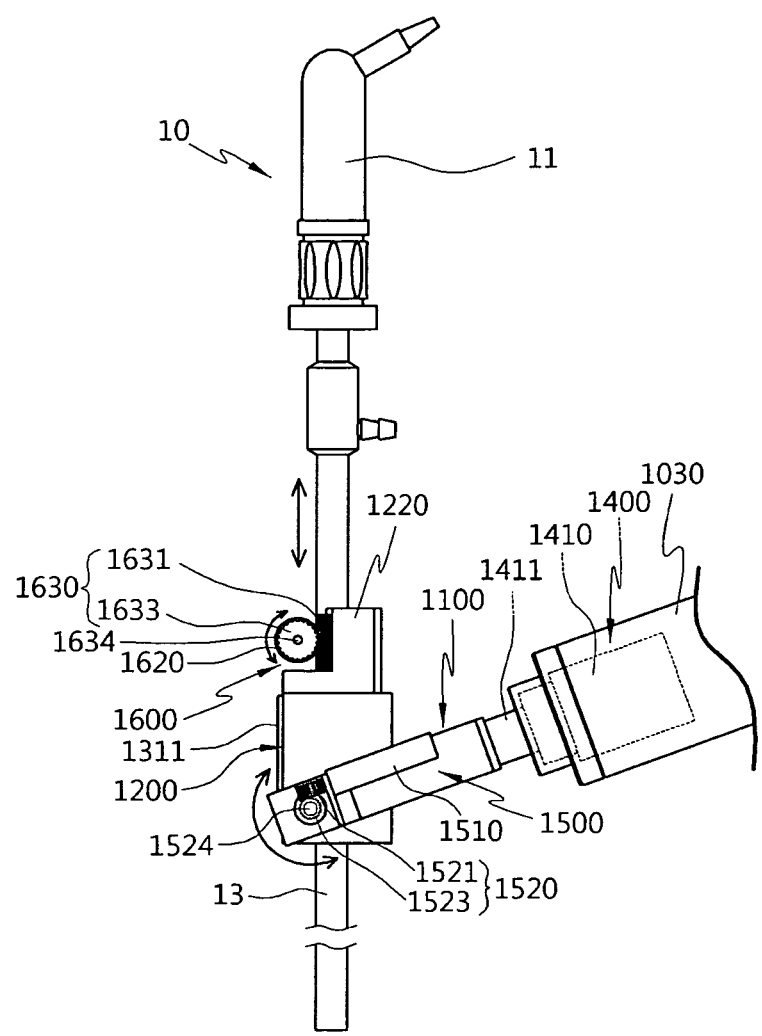
FIG. 7 is a side view of the endoscope manipulator for MIS according to the present invention.

FIG. 1 is a perspective view of an endoscope manipulator for MIS according to a first example embodiment of the present invention, FIG. 2 is an exploded perspective view of the endoscope manipulator for MIS according to the present invention, FIG. 3 is a perspective view specifically showing a second driver of FIG. 1, FIG. 4 is a perspective view specifically showing a third driver of FIG. 1, FIG. 5 is a perspective view specifically showing an endoscope mounting part of a second rotary part of FIG. 1, FIG. 6 is a perspective view specifically showing a one-click attachment part of the second rotary part of FIG. 5, and FIG. 7 is a side view of the endoscope manipulator for MIS according to the present invention.

As shown in FIGS. 1 to 7, an endoscope manipulator 100 for MIS in accordance with an example embodiment of the present invention may include a multi-joint arm 1000, a first rotary part 1100, a second rotary part 1200, a one-click attachment part 1300, a first driver 1400, a second driver 1500, a third driver 1600, etc.

The multi-joint arm 1000 may be constituted by a multi-joint type manual link connected by at least three links. For example, in this example embodiment, the multi-joint arm 1000 is provided as a triaxial link constituted by a base link 1010 rotatably coupled to an arm body 1001, an intermediate link 1020 connected to the base link 1010, and a tip link 1030 connected to the intermediate link 1020 and corresponding to an end of the multi-joint arm 1000, but not limited thereto. The multi-joint arm 1000 may be implemented as various multi-joint structures. Here, the arm body 1001 may be detachably coupled to an operation table (not shown), disposed on a floor near the operation table (not shown), or fixed to a ceiling or a wall near the operation table (not shown). A first motor 1410 configured to rotate the first rotary part 1100, which will be described below, may be installed in a front end of the tip link 1030.

In addition, while not shown, the multi-joint arm 1000 may be configured such that all of the joints can be manually locked or unlocked through adjustment of one lever or screw. That is, the multi-joint arm 1000 of the present invention may be manually locked or unlocked by a user, without controlling movement of all of the joints using motors. Therefore, by reducing the total weight and size of the multi-joint arm 1000, a compact and lightweight endoscope manipulator 100 is possible, and all of the joints of the multi-joint arm 1000 can be manually locked or unlocked to simply adjust a position of the endoscope.

The first rotary part 1100 is coupled to an end of the multi-joint arm 1000 to be rotated about the first rotary shaft a, and rotated by the first driver 1400 to laterally move an endoscope 10 with respect to the first rotary shaft a. Here, the first rotary shaft a corresponds to a rotary shaft 1411 of the first motor 1410 installed in the tip link 1030 of the multi-joint arm 1000 in an axial direction thereof.

In addition, the one end of the first rotary part 1100 is coupled to the rotary shaft 1411 of the first motor 1410 to be rotated about the first rotary shaft a, and the other end is rotatably coupled to the second rotary part 1200 to be rotated about a second rotary shaft b. For example, while the example embodiment illustrates the first rotary part 1100 in which the other end is bifurcated and rotatably coupled to both sides of the second rotary part 1200 to form a U-shape, the structure is not limited thereto, and may include any structure in which the other end of the first rotary part 1100 is rotatably coupled to at least one surface of the second rotary part 1200.

The second rotary part 1200 is coupled to the first rotary part 1100 to be rotated about the second rotary shaft b perpendicular to the first rotary shaft a, and rotated by the second driver 1500 to vertically rotate the endoscope 10 with respect to the second rotary shaft b. Here, the second rotary shaft b corresponds to a rotary shaft 1524 of a worm wheel 1523 of the second driver 1500, which will be described below.

Further, the second rotary part 1200 may include a rotary bracket 1210 coupled to the first rotary part 1100 to be rotated about the second rotary shaft b, an endoscope mounting part 1220 coupled to the rotary bracket 1210 to mount the endoscope 10, and so on. Here, the endoscope 10 is a medical imaging device configured to obtain a visual field of an operation area through minimal incision during MIS and NOTES. A conventional endoscope 10 may include a small charge coupled device (CCD) camera 11, an elongated endoscope tube 13 fastened to the front of the CCD camera 11 and having straightly aligned lenses (not shown) and optical fibers (not shown), an image processor (not shown) and a display part (not shown) configured to output an image obtained through the CCD camera 11 on a screen, and so on. Since the endoscope 10 is already known in the art, detailed description thereof will be omitted.

In this example embodiment, the rotary bracket 1210 has a substantially U-shaped structure such that both sides thereof are coupled to inner sides of the other bifurcated ends of the U-shaped first rotary part 1100 to be rotated by the rotary shaft 1524 of the worm wheel 1523 of the second driver 1500 and the endoscope mounting part 1220 is mounted on an inner side thereof through an open space, but not limited thereto, may have various shapes. In addition, the endoscope mounting part 1220 is mounted on the substantially C-shaped rotary bracket 1210 and coupled thereto, and has a case shape in which the one-click attachment part 1300, a third motor 1610, etc., are installed. Here, the endoscope mounting part 1220 may include a lower surface opened to install a one-click button body 1310, an spring 1320, and the third motor 1610, which will be described later, therein, an upper surface having a button exposure hole 1221 configured to expose a one-click button 1311 of the one-click button body 1310, an endoscope insertion part 1223 formed at front and rear surfaces to expose an endoscope insertion hole 1313 of the one-click button body 1310, and a shaft hole 1225 formed at the rear surface to expose a rotary shaft 1611 of the third motor 1610.

In addition, more specifically, the second rotary part 1200 may include the one-click attachment part 1300 to detachably couple the endoscope 10 to the endoscope mounting part 1220 by one click. Here, the one-click attachment part 1300 may include the one-click button body 1310, onto which the endoscope tube 13 is press-fitted, selectively adhering or separating the endoscope tube 13 to/from a conveyance roller 1620 upon one click through raising/lowering thereof, the elastic member 1320 configured to provide an elastic force to the one-click button body 1310 such that the endoscope tube 13 is adhered to the conveyance roller 1620, and so on. The one-click button body 1310 is installed in the endoscope mounting part 1220, and has a cylindrical shape into which the endoscope insertion hole 1313 is formed in a longitudinal direction so that the endoscope tube 13 is inserted to pass therethrough. In addition, the upper surface of the one-click button body 1310 may be configured to expose the one-click button 1311 through the button exposure hole 1221 of the endoscope mounting part 1220. The elastic member 1320 may include at least one spring (hereinafter, referred to by reference numeral '1320') installed between an outer diameter of the one-click button body 1310 opposite to the conveyance roller 1620 with respect to the endoscope tube 13 and a lower surface of the second rotary part 1200.

The first driver 1400 drives rotation of the first rotary part 1100. Here, the first driver 1400 may include the first motor 1410 installed at an end of the multi-joint arm 1000 to laterally rotate the endoscope 10 with respect to the first rotary shaft a through rotation of the first rotary part 1100. Here, the rotary shaft 1411 of the first motor 1410 corresponds to the first rotary shaft a disposed in a longitudinal direction of the tip link 1030 of the multi-joint aim 1000.

The second driver 1500 drives rotation of the second rotary part 1200. Here, the second driver 1500 vertically rotates the endoscope 10 with respect to the second rotary shaft b through rotation of the second rotary part 1200. Here, the second rotary shaft b is perpendicular to the first rotary shaft a, and corresponds to the rotary shaft 1524 of the worm wheel 1523 of a first gear 1520, which will be described below.

The second driver 1500 may include a second motor 1510, the first gear 1520, and so on. The second motor 1510 is fixed to the first rotary part 1100, and the first gear 1520 may be configured to transmit a rotational force of the second motor 1510 to the second rotary shaft b configured to rotatably pivot the first rotary part 1100 and the second rotary part 1200. In addition, the first gear 1520 may be provided as a first worm gear (hereinafter, referred to by reference numeral '1520') including a worm 1521 installed at a rotary shaft 1511 of the second motor 1510 and the worm wheel 1523 installed at the second rotary shaft b to be engaged with the worm 1521 and rotated therewith. Here, the rotary shaft 1511 of the second motor 1510 is disposed perpendicular to the second rotary shaft b. While the example embodiment illustrates the second driver 1500 as a worm gear, the second driver 1500 is not limited thereto, and may be constituted by a bevel gear (not shown), etc., in which two rotary shafts are perpendicular to each other.

The third driver 1600 may be installed at the second rotary part 1200 to drive straight conveyance of the endoscope 10 inserted into the endoscope mounting part 1220 of the second rotary part 1200.

The third driver 1600 may include the third motor 1610, the conveyance roller 1620, a second gear 1630, and so on. The third motor 1610 is installed in the endoscope mounting part 1220 of the second rotary part 1200 to be parallel to the endoscope insertion hole 1313 of the one-click button body 1310, the conveyance roller 1620 is adhered to an outer diameter of the endoscope tube 13 inserted into the endoscope insertion hole 1313 of the one-click button body 1310 so that both ends of a pair of roller fixing pieces 1227a and 1227b installed at a rear end of the endoscope mounting part 1220 are rotatably installed to straightly convey the endoscope 10, and the second gear 1630 transmits a rotational force of the third motor 1610 to a rotary shaft 1621 of the conveyance roller 1620. Here, the second gear 1630 may be provided as a second worm gear (hereinafter, referred to by reference numeral '1630') including a worm 1631 installed at the rotary shaft 1611 of the third motor 1610, and a worm wheel 1633 installed at the rotary shaft 1621 of the conveyance roller 1620 to be engaged with the worm 1631 and rotated therewith. Here, the rotary shaft 1611 of the third motor 1610 is disposed perpendicular to the rotary shaft 1621 of the conveyance roller 1620. In addition, the rotary shaft 1621 of the conveyance roller 1620 is disposed perpendicular to a conveyance shaft c of the endoscope tube 13. In addition, the conveyance roller 1620 may have a semi-circular groove formed at an outer surface of the conveyance roller 1620 to correspond to an outer periphery of the endoscope tube 13 in order to increase an area of the outer periphery of the endoscope tube 13, smoothly conveying the endoscope tube 13.

The endoscope manipulator 100 for MIS in accordance with an example embodiment of the present invention may continuously adjust the position and viewing direction of the endoscope in order to maximally widely and accurately show the state of the operating area and movement of the surgical instrument in the patient's body, which are prone to change frequently during performance of MIS and NOTES. In order to adjust movement of the endoscope 10 throughout the operation, first, after fixing the arm body 1001 of the multi-joint arm 1000 to the operation table, all of the joints from the base link 1010 to the tip link 1030 are manually manipulated such that the endoscope tube 13 fitted onto the tip part of the multi-joint arm 1000 can be inserted into an incision area of the patient. After adjusting positions of all of the joints of the multi-joint arm 1000, the multi-joint arm 1000 is securely fixed by locking the joints using a single lever or screw. Next, the endoscope 10 mounted on the tip part of the multi-joint arm 1000 is adjusted by the motors 1410, 1510 and 1610 to enable three degrees of freedom of movement, showing the state of the operating area and movement of the surgical instrument in the patient's body, which are prone to change frequently, through minimal incision.

Hereinafter, operations of the endoscope manipulator for MIS in accordance with an example embodiment of the present invention will be described with reference to FIGS. 8 to 14.

Figure 8:
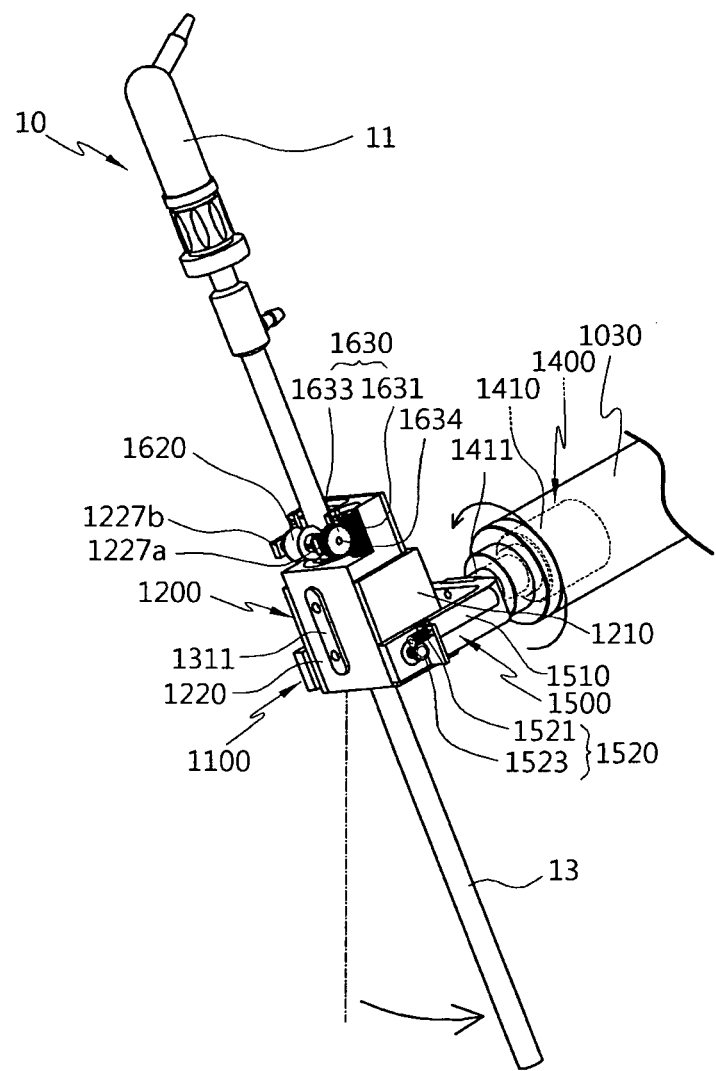
FIGS. 8 and 9 show lateral rotation of an endoscope using the endoscope manipulator for MIS according to the present invention.
Figure 9:
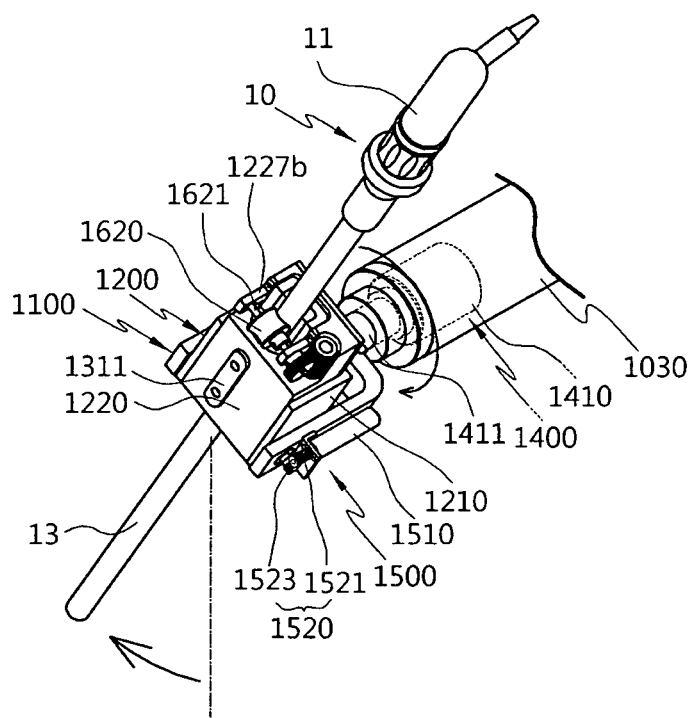

FIGS. 8 and 9 show lateral rotation of an endoscope using the endoscope manipulator for MIS according to the present invention.

First, as shown in FIG. 8, when the first motor 1410 installed at the tip link 1030 of the multi-joint arm 1000 is rotated rightward, i.e., clockwise, the first rotary part 1100 fixed to the rotary shaft 1411 of the first motor 1410 is rotated clockwise. At this time, as the second rotary part 1200 coupled to the first rotary part 1100 is inclined rightward, the end of the endoscope tube 13 press-fitted onto the endoscope mounting part 1220 of the second rotary part 1200 is rotated leftward with respect to the first rotary shaft a.

Next, as shown in FIG. 9, when the first motor 1410 is rotated leftward, i.e., counterclockwise, the first rotary part 1100 fixed to the rotary shaft 1411 of the first motor 1410 is rotated counterclockwise. At this time, as the second rotary part 1200 coupled to the first rotary part 1100 is inclined leftward, the end of the endoscope tube 13 press-fitted onto the endoscope mounting part 1220 of the second rotary part 1200 is rotated rightward with respect to the first rotary shaft a.

Figure 10:
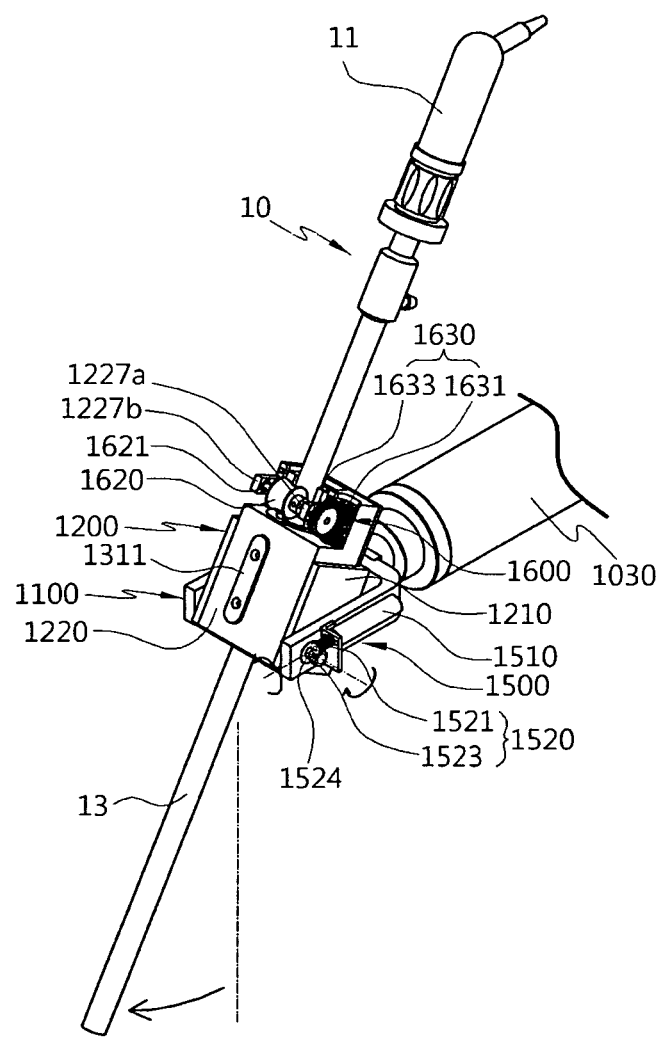
FIGS. 10 and 11 show vertical rotation of the endoscope using the endoscope manipulator for MIS according to the present invention.
Figure 11:
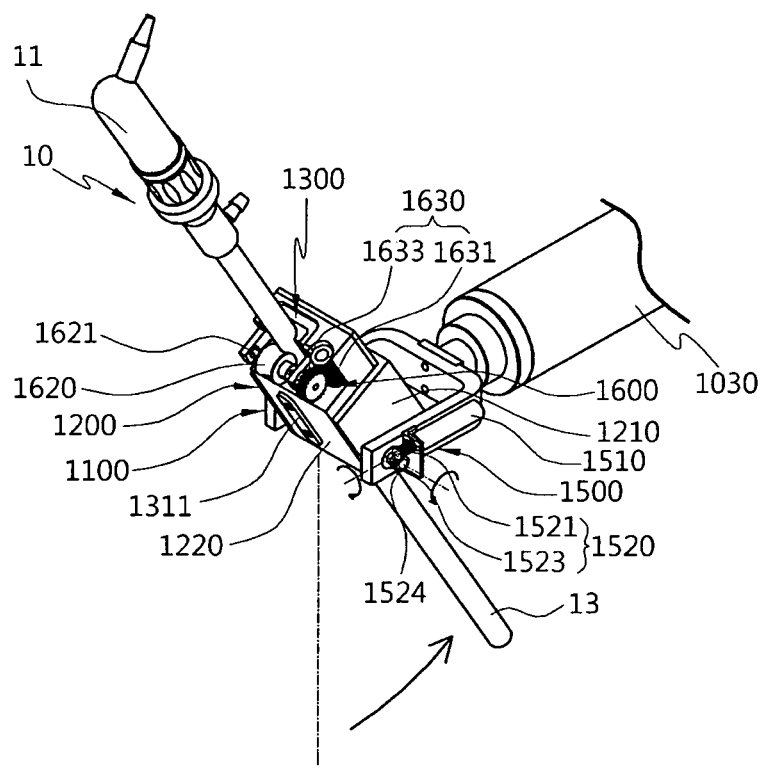

FIGS. 10 and 11 show vertical rotation of the endoscope using the endoscope manipulator for MIS according to the present invention.

First, as shown in FIG. 10, when the second motor 1510 of the second driver 1500 fixed to the first rotary part 1100 is rotated rightward, i.e., clockwise, the worm 1521 fixed to the rotary shaft 1511 of the second motor 1510 is rotated clockwise, and thus, the worm wheel 1523 is engaged with the worm 1521 to be rotated clockwise about the second rotary shaft b. At this time, as the second rotary part 1200 coupled to the rotary shaft 1524 of the worm wheel 1523 is rotated clockwise with respect to the second rotary shaft b, the end of the endoscope tube 13 press-fitted onto the endoscope mounting part 1220 of the second rotary part 1200 is rotated upward with respect to the second rotary shaft b.

Next, as shown in FIG. 11, when the second motor 1510 of the second driver 1500 fixed to the first rotary part 1100 is rotated leftward, i.e., counterclockwise, the worm 1521 fixed to the rotary shaft 1511 of the second motor 1510 is rotated counterclockwise, and thus, the worm wheel 1523 is engaged with the worm 1521 to be rotated counterclockwise about the second rotary shaft b. At this time, as the second rotary part 1200 coupled to the rotary shaft 1524 of the worm wheel 1523 is rotated counterclockwise about the second rotary shaft b, the end of the endoscope tube 13 press-fitted onto the endoscope mounting part 1220 of the second rotary part 1200 is rotated downward with respect to the second rotary shaft b.

Figure 12:
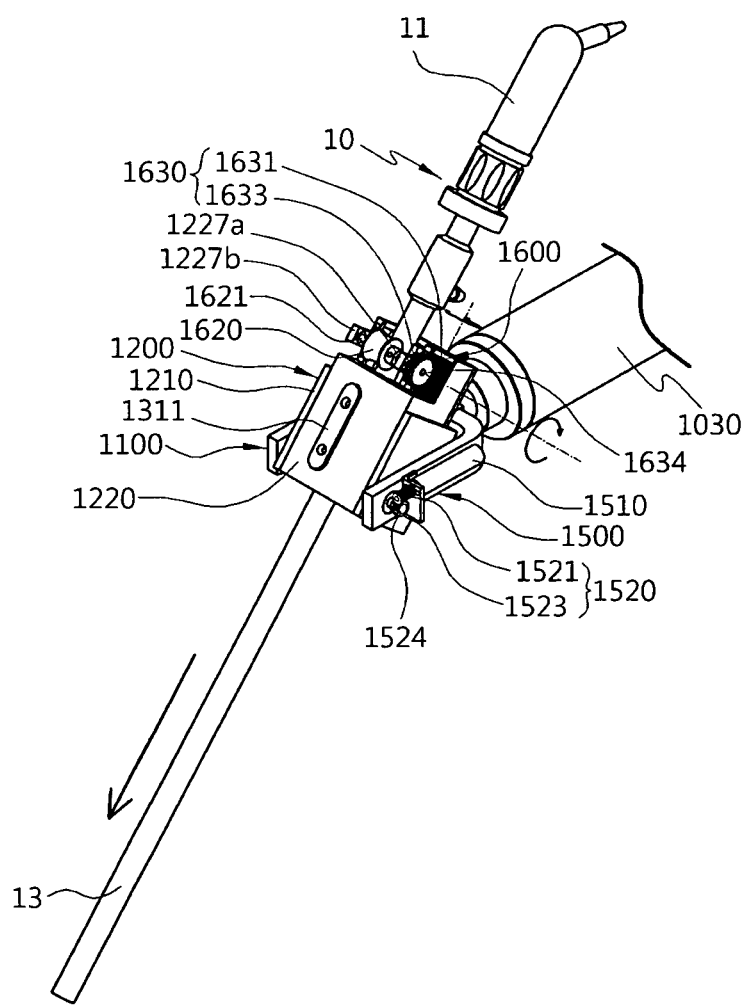
FIGS. 12 and 13 show forward/backward conveyance of the endoscope using the endoscope manipulator for MIS according to the present invention.
Figure 13:
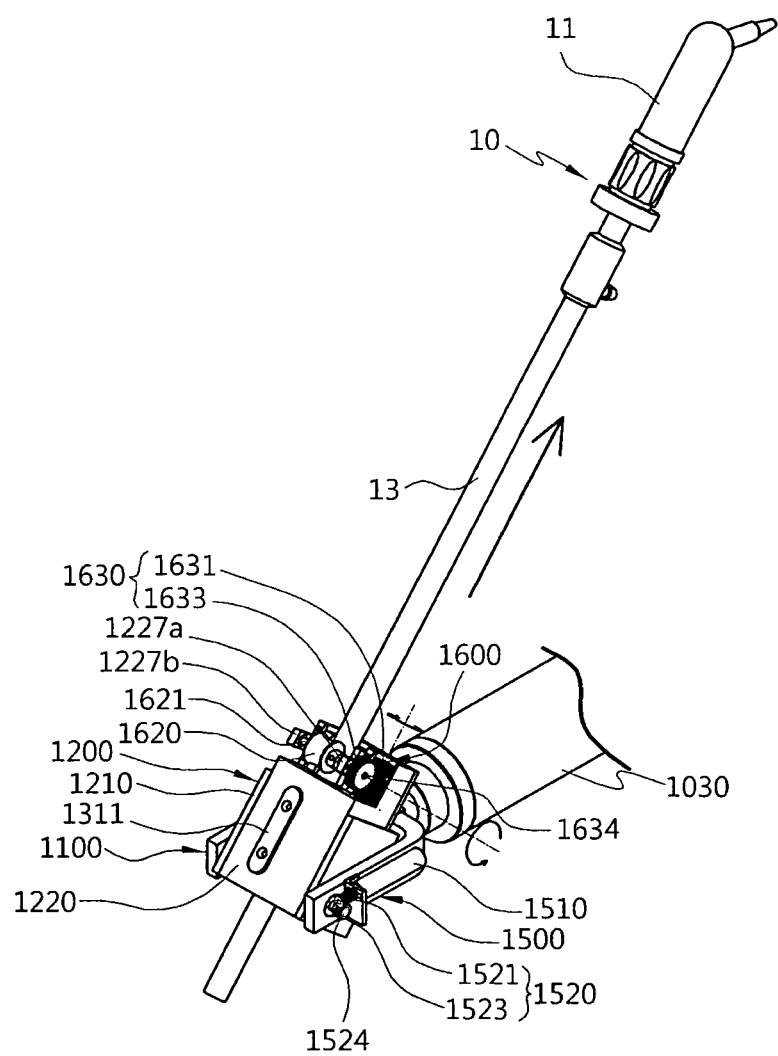

FIGS. 12 and 13 show forward/backward conveyance of the endoscope using the endoscope manipulator for MIS according to the present invention.

First, as shown in FIG. 12, when the third motor 1610 of the third driver 1600 is rotated rightward, i.e., clockwise, in a state in which the endoscope tube 13 is press-fitted into the endoscope insertion hole 1313 of the endoscope mounting part 1220, the worm 1631 fixed to the rotary shaft 1611 of the third motor 1610 is rotated clockwise, and thus, the worm wheel 1633 is engaged with the worm 1631 to be rotated clockwise so that the conveyance roller 1620 coupled to the rotary shaft 1634 of the worm wheel 1633 is also rotated clockwise. At this time, since the conveyance roller 1620 is adhered to the outer diameter of the endoscope tube 13, the conveyance roller 1620 is rotated clockwise to straightly convey the endoscope tube 13 forward.

Next, as shown in FIG. 13, when the third motor 1610 of the third driver 1600 is rotated leftward, i.e., counterclockwise in a state in which the endoscope tube 13 is press-fitted into the endoscope insertion hole 1313 of the endoscope mounting part 1220, the worm 1631 fixed to the rotary shaft 1611 of the third motor 1610 is rotated counterclockwise, and thus, the worm wheel 1633 is engaged with the worm 1631 to be rotated counterclockwise so that the conveyance roller 1620 coupled to the rotary shaft 1634 of the worm wheel 1633 is also rotated counterclockwise. At this time, since the conveyance roller 1620 is adhered to the outer diameter of the endoscope tube 13, the conveyance roller 1620 is rotated counterclockwise to straightly convey the endoscope tube 13 backward.

Figure 14:
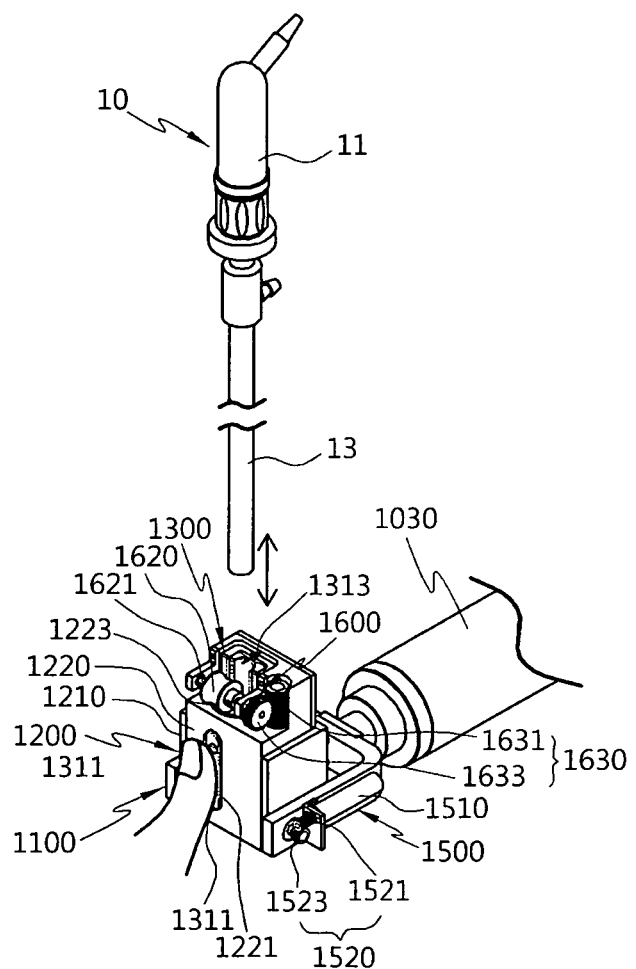
FIG. 14 shows one-click attachment of the endoscope of the endoscope manipulator for MIS according to the present invention.

FIG. 14 shows one-click attachment of the endoscope of the endoscope manipulator for MIS according to the present invention.

As shown in FIG. 14, since the endoscope mounting part 1220 includes the one-click attachment part 1300, it is possible to readily release and insert the endoscope 10 through one click. More specifically, if blood is stuck to the endoscope lens during operation, when the one-click button 1311 is pressed, the spring 1320 installed in the endoscope mounting part 1220 is compressed, and thus, the one-click button body 1310 is lowered so that the endoscope tube 13 press-fitted into the endoscope insertion hole 1313 of the one-click button body 1310 is also lowered. At this time, as the endoscope tube 13 is released from the conveyance roller 1620 to be spaced apart therefrom, the endoscope tube 13 can be readily separated from the endoscope mounting part 1220. After rapidly and readily separating the endoscope tube 13 and cleaning the blood, when the endoscope tube 13 is inserted into the endoscope insertion hole 1313 of the endoscope mounting part 1220 and the one-click button 1311 is released from a pressed state, the one-click button body 1310 is raised by a recovery force due to expansion of the spring 1320, and thus, the endoscope tube 13 is adhered to the conveyance roller 1620 again, thereby readily and rapidly mounting the endoscope 10 thereon.

In addition, while not shown, a surgeon may directly manipulate the triaxial movement for vertical, lateral and forward/backward conveyance of the endoscope tube 13 using a foot pedal or joystick connected to a controller configured to control the respective motors 1410, 1510 and 1610 of the first driver 1400, the second driver 1500 and the third driver 1600. In addition, a motor (not shown) may be further installed at the endoscope mounting part 1220 to rotate the endoscope tube 13 about the conveyance shaft c of the endoscope tube 13 as a rotary shaft.

Figure 15:
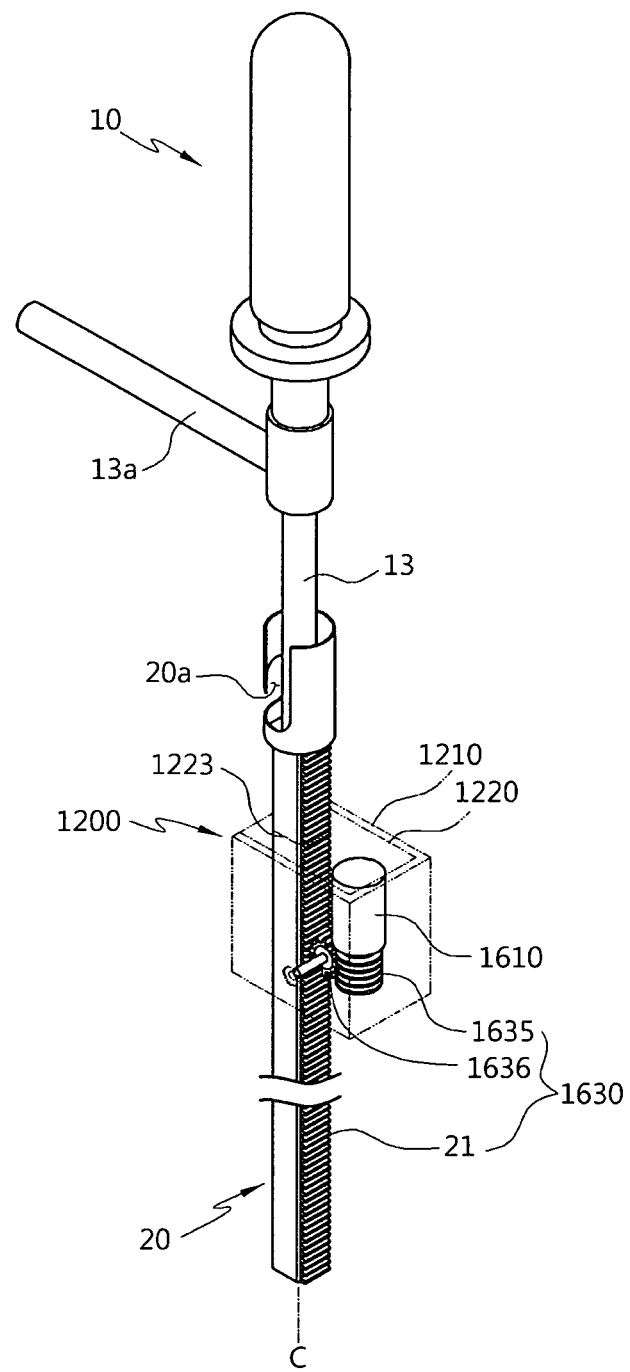
FIG. 15 is a perspective view of a third driver of an endoscope manipulator for MIS according to another example embodiment of the present invention.

FIG. 15 is a perspective view of a third driver of an endoscope manipulator for MIS according to another example embodiment of the present invention.

As shown in FIG. 15, a third driver 1600 drives forward/backward straight conveyance of the endoscope 10 inserted into the endoscope mounting part 1220 of the second rotary part 1200.

The third driver 1600 may include a third motor 1610, a second gear 1630, and an endoscope conveyance tube 20. The third motor 1610 is installed at the endoscope mounting part 1220 of the second rotary part 1200 to be parallel to the endoscope insertion part 1223. Here, the endoscope insertion part 1223 has an elliptical or polygonal cross-section corresponding to the cross-section of the endoscope conveyance tube 20, which will be described below, and passes through the endoscope mounting part 1220 forward and backward. The endoscope conveyance tube 20 is configured such that the endoscope tube 13 is inserted therethrough, and has a fastening groove 20a formed at a rear end of the endoscope conveyance tube 20 such that a fastening projection 13a of the endoscope tube 12 is inserted and rotated to be fastened thereto. The endoscope conveyance tube 20 is straightly movably inserted into the endoscope insertion part 1223 of the second rotary part 1200 forward and backward. Here, the endoscope conveyance tube 20 may have an elliptical or polygonal cross-section such that the endoscope conveyance tube 20 is not laterally rotated about a forward/backward moving shaft C when the endoscope conveyance tube 20 straightly moves. The second gear 1630 transmits a rotational force of the third motor 1610 to straightly move the endoscope conveyance tube 20. For this purpose, the second gear 1630 may include a rack gear 21 formed at an outer diameter of the endoscope conveyance tube 20 in a longitudinal direction thereof, and a pinion gear installed at a rotary shaft of the third motor 1610 to be engaged and rotated with the rack gear 21. Here, the pinion gear may include a first gear 1635 installed at the rotary shaft of the third motor 1610, and a second gear 1636 installed between the first gear 1635 and the rack gear 21.

As described above, according to the endoscope manipulator 100 for MIS in accordance with an example embodiment of the present invention, the multi-joint arm 1000 is configured so that movement of all of the joints from the base link 1010 to the tip link 1030 is manually locked-unlocked by a user and not controlled by motors. In addition, the endoscope 10 mounted on an end of the multi-joint arm 1000 is manipulated using the motors 1410, 1510 and 1610 to enable movement of three degrees of freedom, thereby accomplishing the compact and light weight endoscope manipulator 100. In addition, the endoscope tube 13 can be press-fitted onto the tip part of the multi-joint arm 1000, and a triaxial movement function for vertical, lateral and forward/backward conveyance of the endoscope tube 13 is implemented in the tip part of the multi-joint arm 1000. As a result, since external joints are not moved during the operation, it is possible to minimize disturbance or restriction to activities of medical staff. In addition, when blood is stuck to an endoscope lens during operation, in order to rapidly release the endoscope 10 from the tip part and clean and insert the endoscope 10 into the tip part again, a one-click button function can be added to improve convenience of use.

In an endoscope manipulator for MIS in accordance with an example embodiment of the present invention, a multi-joint arm is configured so that movement of all of the joints from a base link to a tip link is manually locked-unlocked by a user and not controlled by motors. In addition, the endoscope mounted on an end of the multi-joint arm is manipulated using motors to enable movement of three degrees of freedom, thereby accomplishing a compact and light weight endoscope manipulator.

In addition, a tube of the endoscope can be press-fitted onto a tip part of the multi-joint arm, and a triaxial movement function for vertical, lateral and forward/backward conveyance of the endoscope is implemented in the tip part of the multi-joint arm. As a result, since external manual joints are not moved during the operation, it is possible to minimize disturbance or restriction to activities of medical staff.

Further, only a fastening part of the tip part of the multi-joint arm constituted by the external manual joints is partially modified to modularize the triaxial control tip and the multi-joint arm so that it can have various lengths and shapes depending on the kinds of operations.

Furthermore, a triaxial control tip appropriate to the kinds of the endoscope used in medical institutions is provided and various triaxial control tips can be exchanged to a single multi-joint arm so that a single standardized multi-joint arm and several individual triaxial control tips are provided as a set to allow doctors to use various endoscopes according to personal preferences.

In addition, when blood is stuck to an endoscope lens during operation, in order to rapidly release the endoscope from the tip part and clean and insert the endoscope into the tip part again, a one-click button function can be added to improve convenience of use.

While the invention has been shown and described with reference to certain example embodiments thereof, it will be understood by those skilled in the art that various changes in form and details may be made therein without departing from the spirit and scope of the invention as defined by the appended claims.

What is claimed is:

1. An endoscope manipulator for minimally invasive surgery, comprising:
    a multi-joint arm;
    a first rotary part coupled to an end of the multi-joint arm to be rotated about a center of a first rotary shaft;
    a first driver configured to drive rotation of the first rotary part;
    a second rotary part coupled to the first rotary part to be rotated about a second rotary shaft perpendicular to the first rotary shaft, and having an endoscope mounted thereon;
    a second driver configured to drive rotation of the second rotary part; and
    a third driver configured to drive straight conveyance of the endoscope press-fitted onto the second rotary part,
    wherein the third driver comprises:
    a third motor installed at the second rotary part;
    an endoscope conveyancing part installed at the second rotary part; and
    a second gear configured to transmit a rotational force of the third motor to the endoscope conveyancing part.

2. The endoscope manipulator according to claim 1, wherein the multi-jointarm is provided as a multi-joint type manual link.

3. The endoscope manipulator according to claim 1, wherein one end of the first rotary part is coupled to the first driver to be rotated about the first rotary shaft, and the other end of the first rotary part is coupled to the second rotary part to be rotated about the second rotary shaft.

4. The endoscope manipulator according to claim 1, wherein the first driver comprises a first motor installed at an end of the multi joint arm, and configured to laterally rotate the endoscope with respect to the first rotary shaft through rotation of the first rotary part.

5. The endoscope manipulator according to claim 1, wherein the second rotary part comprises:
    a rotary bracket coupled to the first rotary part to be rotated about the second rotary shaft; and
    an endoscope mounting part coupled to the rotary bracket and on which the endoscope is mounted.

6. The endoscope manipulator according to claim 1, wherein the second driver rotates the endoscope in a vertical direction with respect to the second rotary shaft through rotation of the second rotary part.

7. The endoscope manipulator according to claim 6, wherein the second driver comprises:
    a second motor installed at the first rotary part; and
    a first gear configured to transmit a rotational force of the second motor to the second rotary shaft configured to rotatably pivot the first rotary part and the second rotary part.

8. The endoscope manipulator according to claim 7, wherein the first gear is a first worm gear including a worm installed at a rotary shaft of the second motor, and a worm wheel installed at the second rotary shaft to be engaged with the worm and rotated therewith.

9. The endoscope manipulator according to claim 8, wherein the rotary shaft of the second motor is disposed perpendicular to the second rotary shaft.

10. The endoscope manipulator according to claim 1,
    wherein the endoscope conveyancing part is a conveyance roller rotatably installed at the second rotary part and adhered to a tube of the endoscope to straightly convey the endoscope forward and backward, and
    wherein the second gear is configured to transmit a rotational force of the third motor to a rotary shaft of the conveyance roller.

11. The endoscope manipulator according to claim 10, wherein the second gear is a second worm gear including a worm installed at a rotary shaft of the third motor, and a worm wheel installed at the rotary shaft of the conveyance roller to be engaged with the worm and rotated therewith.

12. The endoscope manipulator according to claim 11, wherein the rotary shaft of the third motor is disposed perpendicular to the rotary shaft of the conveyance roller.

13. The endoscope manipulator according to claim 10, wherein the second rotary part comprises a one-click attachment part to which the endoscope is detachably attached by one click.

14. The endoscope manipulator according to claim 13, wherein the one-click attachment part comprises:
    a one-click button body, onto which the tube of the endoscope is press-fitted, configured to selectively adhere or separate the tube of the endoscope to or from the conveyance roller upon one-click operation through raising/lowering thereof; and
    an elastic member configured to provide an elastic force to the one-click button body so that the tube of the endoscope is closely adhered to the conveyance roller.

15. The endoscope manipulator according to claim 14, wherein the one-click button body is installed in the second rotary part, and has a cylindrical shape having an endoscope insertion hole formed in a longitudinal direction thereof so that the tube of the endoscope is press-fitted thereinto and an upper surface partially exposed from the second rotary part.

16. The endoscope manipulator according to claim 14, wherein the elastic member comprises at least one spring disposed between an outer diameter of the one-click button body positioned at an opposite side of the conveyance roller with respect to the tube of the endoscope and a lower surface of the second rotary part.

17. The endoscope manipulator according to claim 1,
    wherein the endoscope conveyancing part is an endoscope conveyance tube, in which a tube of the endoscope is inserted and fastened, movably installed at the second rotary part forward and backward, and
    wherein the second gear is configured to transmit a rotational force of the third motor to straightly move the endoscope conveyance tube.

18. The endoscope manipulator according to claim 17, wherein the endoscope conveyance tube has an elliptical or polygonal cross-section.

19. The endoscope manipulator according to claim 17, wherein the second gear comprises:
   a rack gear formed at an outer diameter of the endoscope conveyance tube in a longitudinal direction thereof; and
   a pinion gear installed at a rotary shaft of the third motor to be engaged and rotated with the rack gear.

\* \* \* \* \*

UNITED STATES PATENT AND TRADEMARK OFFICE
CERTIFICATE OF CORRECTION

PATENT NO.         : 8,460,175 B2
APPLICATION NO.    : 12/589439
DATED              : June 11, 2013
INVENTOR(S)        : Yung-Ho Jo et al.

Page 1 of 1

It is certified that error appears in the above-identified patent and that said Letters Patent is hereby corrected as shown below:

In the Claims:

In Column 11, Claim 2, line 44 delete "multi-jointarm" and insert --multi-joint arm--

In Column 11, Claim 4, line 53 delete "multi joint arm" and insert --multi-joint arm--

Signed and Sealed this
Third Day of September, 2013

Teresa Stanek Rea
*Acting Director of the United States Patent and Trademark Office*